(12) United States Patent
Den Boestert et al.

(10) Patent No.: US 7,501,062 B2
(45) Date of Patent: Mar. 10, 2009

(54) PROCESS FOR PERMEATION ENHANCED REACTIVE EXTRACTION OF LEVULINIC ACID

(75) Inventors: Johannes Leendert Willem Cornelis Den Boestert, Amsterdam (NL); Johannes Pieter Haan, Amsterdam (NL); Arian Nijmeijer, Amsterdam (NL)

(73) Assignee: Shell Oil Company, Houston, TX (US)

( * ) Notice: Subject to any disclaimer, the term of this patent is extended or adjusted under 35 U.S.C. 154(b) by 517 days.

(21) Appl. No.: 11/357,229

(22) Filed: Feb. 17, 2006

(65) Prior Publication Data

US 2006/0201879 A1  Sep. 14, 2006

(30) Foreign Application Priority Data

Feb. 22, 2005  (EP)  ................................. 05101341

(51) Int. Cl.
*B01D 11/04* (2006.01)
*B01D 61/00* (2006.01)

(52) U.S. Cl. ...................... 210/638; 210/634; 210/639; 210/651; 560/174; 560/155; 562/577

(58) Field of Classification Search ........................ None
See application file for complete search history.

(56) References Cited

U.S. PATENT DOCUMENTS

| | | | | |
|---|---|---|---|---|
| 2,029,412 | A | 2/1936 | Cox et al. | 260/106 |
| 4,442,303 | A | 4/1984 | Mims | 560/191 |
| 4,476,025 | A | 10/1984 | Chum et al. | 210/638 |
| 5,562,777 | A | 10/1996 | Farone et al. | 127/37 |
| 5,892,107 | A | 4/1999 | Farone et al. | 562/515 |
| 6,054,611 | A | 4/2000 | Farone et al. | 562/515 |
| 7,378,549 | B2 | 5/2008 | Ayoub | 562/577 |
| 2003/0233011 | A1* | 12/2003 | Fagan et al. | 560/174 |
| 2006/0047139 | A1 | 3/2006 | Ayoub | 560/155 |
| 2006/0201879 | A1 | 9/2006 | Den Boestert et al. | 210/634 |

FOREIGN PATENT DOCUMENTS

| | | |
|---|---|---|
| EP | 1304320 A2 | 4/2003 |
| EP | 1304320 A3 | 8/2003 |
| GB | 1282926 | 7/1972 |
| WO | 89/10362 | 11/1989 |
| WO | 96/40609 | 12/1996 |
| WO | 97/47579 | 12/1997 |
| WO | 98/19986 | 5/1998 |
| WO | 03/085071 | 10/2003 |
| WO | WO2005070867 | 8/2005 |

OTHER PUBLICATIONS

H. Kropf: "Houben-Weyl, Methoden der organischen chemie, Teil 1, Band 6/1a" 1980, G. Thieme Verlag, Stuttgart, XP002286016 p. 2, see entry 2-Methyl-propanol and p. 4, see entries of diols.
European Patent Office Communication dated Aug. 24, 2005 including European Search Report dated Jul. 21, 2005 for application No. EP05101341.
European Patent Office Communication dated Jul. 12, 2004 including European Search Report dated Jun. 25, 2004 for application No. EP 04100272.
PCT International Search Report, International Application No. PCT/EP2005/050316, filed Jan. 26, 2005.
PCT Written Opinion of the International Searching Authority, International Application No. PCT/EP2005/050316, filed Jan. 26, 2005.
U.S. Appl No. 11/041,324, filed Jan. 24, 2005.

* cited by examiner

*Primary Examiner*—Krishnan S Menon

(57) ABSTRACT

A process for permeation enhanced reactive extraction of levulinic acid from a liquid aqueous phase comprising levulinic acid, wherein the levulinic acid from the aqueous phase is brought into contact with a liquid alcohol phase at esterification conditions in the presence of a catalyst at a temperature in the range of from 50 to 250° C., the aqueous phase and the alcohol phase being separated from each other by a membrane, and an aqueous stream depleted in levulinic acid and an alcohol stream comprising ester of levulinic acid are formed.

20 Claims, No Drawings

US 7,501,062 B2

PROCESS FOR PERMEATION ENHANCED REACTIVE EXTRACTION OF LEVULINIC ACID

CROSS-REFERENCE TO RELATED APPLICATIONS

This application claims priority from European Patent Application No. 05101341.5, filed on Feb. 22, 2005, which is incorporated herein by reference. This application is related to U.S. application Ser. No. 11/041,324 filed Jan. 24, 2005.

FIELD OF THE INVENTION

The present invention relates to a process for permeation enhanced reactive extraction of levulinic acid from a liquid aqueous phase.

BACKGROUND OF THE INVENTION

Levulinate esters are known to be useful as plasticisers and solvents and have been suggested as fuel additives. Levulinic acid can be obtained by acid hydrolysis of cellulose-containing biomass or sugars derived therefrom. Such acid hydrolysis processes are known in the art, for example from WO 89/10362, WO 96/40609, U.S. Pat. Nos. 5,892,107 and 6,054,611. Such acid hydrolysis processes yield an aqueous mixture comprising levulinic acid, formic acid, furfural (if $C_5$-sugars containing hemicelluloses were present in the starting material), and the mineral acid that was used as catalyst for the hydrolysis. In the art, several processes for the preparation of levulinate esters starting from such aqueous mixture obtained by acid hydrolysis of biomass are described.

In U.S. Pat. No. 2,029,419 is disclosed the preparation of 2-methylbutyllevulinate ester by esterifying a concentrated, levulinic acid containing syrup obtained from acid hydrolysis of cane sugar with 2-methylbutanol. Water is removed during the esterification process. After the esterification process has been stopped, alcohol is distilled off. The ester is recovered by vacuum distilling the remaining mixture. In the process of U.S. Pat. No. 2,029,419, the amount of water present during the esterification process is very low, since the starting material is a concentrated syrup and water is removed during the esterification process. Disadvantages of the process are that a large amount of energy is needed for water evaporation and that the mineral acid will remain in the product ester stream.

In WO 98/19986 is disclosed the preparation of a levulinate ester by adding methyl or ethyl alcohol to an aqueous levulinic acid/sulphuric acid mixture and refluxing the resulting mixture. The amount of alcohol is in stoichiometric excess to the amount of levulinic acid. It is mentioned that the levulinate ester can be recovered by phase separation after the excess alcohol is distilled off. Separation of the ester from the resulting mixture by means of chromatography is also mentioned.

In WO 97/47579 is disclosed a process for the separation of levulinic acid from a reaction mixture of water-soluble components wherein the levulinic acid is first esterified with an alcohol to produce a water insoluble ester. The ester is then separated from the reaction mixture and subsequently hydrolysed to yield the acid and the alcohol. The alcohol is present in stoichiometric excess to the amount of levulinic acid. The formation and hydrolysis of methyl levulinate is exemplified.

In GB 1,282,926 is disclosed a process wherein an aqueous, levulinic acid-containing solution is contacted with a water-miscible esterifying solvent to form an esterifying mixture. The esterifying mixture is simultaneously contacted with a water-immiscible organic solvent to extract the esters formed. The water-miscible esterifying solvent is preferably a lower alkyl alcohol having one to five carbon atoms and the water-immiscible organic solvent is preferably benzene or chloroform.

In WO 03/085071 is disclosed a process for the preparation of a mixture comprising levulinic acid esters and formic acid esters from biomass, wherein a reaction mixture comprising levulinic acid and formic acid is contacted with an olefin to form an organic phase containing the levulinic acid esters and formic acid esters and an aqueous phase. The olefin is preferably contacted with the reaction mixture in the presence of a water-immiscible hydrocarbon solvent.

The prior art processes of WO 98/19986, WO 97/47579, GB 1,282,926 and WO 03/085071 have several disadvantages. In the processes such as disclosed in WO 98/19986 and WO 97/47579, an aqueous reaction mixture is obtained that contains a relatively high concentration of organic compounds including furfural. As a consequence, the aqueous mixture has to be treated before it could be recycled, since the presence of furfural in the acid reaction mixture may result in the formation of undesired, tar-like by-products. In the processes as disclosed in GB 1,282,926 and WO 03/085071, the esters are extracted from the reaction mixture during or after esterification by means of a water-immiscible solvent. In these processes both an esterifying agent and an extracting solvent are used. This means that both the solvent and the excess of esterifying agent have to be removed from the product streams if the esters are to be obtained in pure form.

SUMMARY OF THE INVENTION

It has now been found that levulinate esters can be prepared and separated from an aqueous phase containing levulinic acid by permeation enhanced reactive extraction, wherein the levulinic acid from the aqueous phase is contacted with a liquid alcohol phase comprising an alcohol that serves both as esterifying alcohol and as extractant for the levulinate ester formed and wherein the aqueous phase and the alcohol phase are separated from each other by a membrane.

Accordingly, the present invention relates to a process for permeation enhanced reactive extraction of levulinic acid from a liquid aqueous phase comprising levulinic acid, wherein the levulinic acid from the aqueous phase is brought into contact with a liquid alcohol phase at esterification conditions in the presence of a catalyst at a temperature in the range of from 50 to 250° C., the aqueous phase and the alcohol phase being separated from each other by a membrane, and an aqueous stream depleted in levulinic acid and an alcohol stream comprising ester of levulinic acid are formed.

An advantage of the novel process is that esterification and separation of the ester from the aqueous phase are combined in a single reactive extraction step without the need for an additional extractant. The alcohol that is already present as esterifying agent also serves as extractant for the levulinate ester.

A further advantage is that even water-miscible alcohols can be used as extractant for the levulinate ester, since the aqueous phase and the alcohol phase are kept separated from each other by means of the membrane.

Another advantage of the novel process is that a great part of the furfural, which is typically present in an aqueous phase comprising levulinic acid that is obtained from acid hydrolysis of biomass, moves into the alcohol phase. As a consequence, the formation of undesired furfural by-products is minimised.

A further advantage is that the permeation enhanced reactive extraction process of the invention can be carried out on an aqueous reaction mixture obtained by acid hydrolysis from biomass, without the need to remove the acid catalyst used in the hydrolysis. The same acid catalyst that is used in the acid hydrolysis process for the preparation of levulinic acid can be used in the permeation enhanced reactive extraction process of the invention. A still further advantage is that the aqueous stream depleted in levulinic acid that is obtained in the reactive extraction process of the invention has a relatively low level of organic compounds. Therefore, the aqueous stream depleted in levulinic acid can be recycled to a levulinic acid-forming acid hydrolysis step for re-use of the acid catalyst. Neutralisation of the acid catalyst is thus not needed. If the acid catalyst is sulphuric acid, the formation of gypsum which is formed upon neutralisation of sulphuric acid with lime, is avoided.

DETAILED DESCRIPTION OF THE INVENTION

In the process according to the invention, levulinic acid is extracted by permeation enhanced reactive extraction from an aqueous phase. The aqueous phase comprising the levulinic acid is preferably an aqueous mixture as obtained after acid hydrolysis of biomass or of $C_6$ sugars derived from biomass. Reference herein to biomass is to lignocellulosic or cellulosic material comprising cellulose, optionally in combination with hemicellulose or lignin. Acid hydrolysis processes wherein $C_6$ sugars or biomass are converted into levulinic acid and formic acid are known in the art, for example from WO 89/10362, WO 96/40609, U.S. Pat. Nos. 5,892,107 and 6,054,611. Furfural is also formed when the starting material contains $C_5$-sugars or hemicelluloses comprising $C_5$-sugars. The hydrolysis is catalysed by a homogeneous acid catalyst, typically sulphuric acid. The hydrolysate is typically separated into a solid fraction comprising lignin residue and unreacted polysaccharides and a liquid fraction. This liquid fraction typically comprises levulinic acid, formic acid, furfural and acid catalyst. This liquid fraction is very suitable as the starting aqueous phase of the process according to the present invention. No further concentration or separation steps are needed.

The aqueous phase preferably comprises 1 to 25 wt % levulinic acid based on the total weight of the aqueous phase, more preferably 2 to 20 wt %.

In the process according to the invention, the liquid aqueous phase comprising levulinic acid is brought into contact with one side (retentate side) of a membrane whilst a liquid alcohol phase is brought into contact with the other side (permeate side) of the membrane. The membrane keeps the two phases separated from each other. The membrane is at least permeable to levulinic acid, such that the levulinic acid from the aqueous phase contacts the alcohol phase. In the process, the levulinic acid is brought into contact with the alcohol phase at esterification conditions and in the presence of a catalyst.

The alcohol phase comprises one or more alcohols. The alcohol phase preferably comprises less than 10 wt % of non-alcohol components, more preferably less than 5 wt %. The alcohol phase may comprise water-miscible or water-immiscible alcohols or a combination thereof. Preferably, the alcohol phase comprises at least 95 wt % of a single alcohol, more preferably it comprises a single alcohol. Preferably, the alcohol phase comprises an alkyl alcohol having at most 12 carbon atoms, more preferably ethanol, 1-butanol, 1-pentanol, 1-or 2-hexanol, 2-ethylhexan-1-ol, or 1-decanol.

The membrane may be any membrane that is able to keep the aqueous phase and the alcohol phase separated whilst it is permeable to at least levulinic acid and that is chemically resistant to the aqueous and the alcohol phase under the reaction conditions applied. The membrane may consist of a single membrane layer or may be a composite of more than one membrane layers or of a porous support layer and one or more membrane layers. The membrane layers may be porous or dense membrane layers and may be hydrophilic or hydrophobic. A porous support layer is typically applied in combination with a dense membrane layer.

In order to bring the levulinic acid from the aqueous phase in contact with the alcohol phase, the membrane is permeable to levulinic acid.

In case the alcohol(s) in the alcohol phase is/are water-immiscible alcohols, reactive extraction of levulinic acid from the aqueous phase could also be performed without a membrane between the aqueous and the alcohol phase. An advantage, however, of keeping the phases separated by means of a membrane is that the formation of an emulsion of the two phases is prevented. Moreover, a large contact area between the two phases can be created whilst preventing emulsion formation.

Reference herein to a water-immiscible alcohol is to an alcohol that has a solubility in water of less than 15 grams per 100 ml at 20° C. This means that the alcohol has at least four carbon atoms. Certain alcohols with at least four carbon atoms are however miscible with water, e.g. 2-methylpropan-2-ol (tert.-butanol), butane-1,4-diol, butane-2,3-diol, and pentane-1,5-diol.

In the case of an alcohol phase with only water-immiscible alcohols, the membrane is preferably a porous membrane, more preferably a porous hydrophilic membrane. Reference herein to a porous membrane is to a membrane of which all layers are porous, i.e. a membrane without a dense layer. Reference herein to a hydrophilic membrane is to a membrane of which all layers are hydrophilic, i.e. without a hydrophobic layer.

Examples of suitable porous hydrophobic membranes include porous polyethylene, porous polypropylene, polysulphone, polyimide, PDVF (polyvinylidenedifluoride), or PTFE (polytetrafluoroethylene). Suitable porous hydrophilic membranes include ceramic membranes, porous glass, porous metal membranes, or porous polymeric membranes such as polyamide, modified cellulose or polyethersulphone or cellulose acetate.

In case of an alcohol phase with only water-immiscible alcohols and a porous membrane, the two phases, i.e. the aqueous and the alcohol phase, will contact and form an interface in the pores or at one of the membrane surfaces. At the interface between the aqueous and the alcohol phase, alcohol from the alcohol phase will react with levulinic acid from the aqueous phase to form an ester of levulinic acid and water. The ester will be extracted to the alcohol phase. Preferably, the interface is created at the membrane surface at the alcohol phase side, i.e. the aqueous phase is present inside the membrane, since this facilitates extraction of the ester into the alcohol phase.

For hydrophilic membranes, it is preferred that the pressure of the alcohol phase is slightly higher than that of the aqueous phase, in order to prevent break-through of the membrane barrier from the aqueous phase side into the alcohol phase side. For hydrophilic membranes, the alcohol phase preferably has a pressure that is 1 to 10 bar, more preferably 1.5 to 3 bar, higher than the pressure of the aqueous phase.

In case the alcohol phase comprises a water-miscible alcohol, the membrane comprises a layer that is more permeable to levulinic acid than to water, preferably a layer that is impermeable to water. Therefore, the membrane preferably comprises a hydrophobic layer that is permeable to levulinic acid, more preferably a dense hydrophobic layer. A membrane comprising a hydrophilic support layer and a dense hydrophobic membrane layer is particularly preferred. In that case, the support layer is preferably located at the aqueous phase side of the membrane (retentate side) and the dense hydrophobic layer at the alcohol phase side of the membrane (permeate side).

Examples of suitable dense hydrophobic membrane layers are silicone rubber-based membranes, in particular polysiloxane membranes such as polydimethylsiloxane, preferably cross-linked polydimethylsiloxane.

If a porous membrane layer is used, the relative pore diameters are typically in the range of from 0.01 to 6 µm, preferably 0.1 to 2 µm, whereby the pores may have any form, for instance round or slit-shaped. The membrane porosity is typically in the range of from 25 to 90%.

Dense membranes are defined as membranes through which compounds are transferred via the solution-diffusion mechanism.

The membrane may be used in any configuration known in the art, for example spiral wound, as hollow fibres or flat sheets. Preferably a hollow fibre membrane unit is used in the process according to the invention.

The aqueous phase and the alcohol phase may flow with respect to each other counter-currently, co-currently, or in cross-current flow. For obtaining maximum conversion of levulinic acid into levulinate ester, it is preferred that the aqueous phase and the alcohol phase are brought into contact with each other in cross-current flow.

The ratio of the flows of the aqueous and the alcohol phase is such that the amount of alcohol that is left after conversion of the levulinic acid into its ester is sufficient for extracting the ester. Preferably, the amount of alcohol supplied to the process is at least two times the amount of levulinic acid supplied to the process, more preferably at least three times. Preferably, the ratio of the mass flow of the alcohol phase and the mass flow of the aqueous phase is in the range of from 1:50 to 1:2, more preferably of from 1:30 to 1:3.

The process conditions are such that esterification takes place and that the levulinate ester formed dissolves into the alcohol phase. Thus, an aqueous stream having a reduced levulinic acid content as compared to the starting aqueous phase and an alcohol stream comprising alcohol and levulinate ester are formed. If furfural is present in the starting aqueous phase, furfural will typically be extracted from the aqueous phase to the alcohol phase.

A catalyst is present to catalyse the esterification reaction. Any catalysts known to be suitable for esterification reactions may be used. Such catalysts are known in the art. The catalyst may be an homogeneous catalyst or an heterogeneous catalyst. Preferably, the catalyst is an acid catalyst, more preferably a homogeneous acid catalyst, even more preferably a mineral acid or a sulphonic acid, for example sulphuric acid, p-toluene sulphonic acid, phosphoric acid, and nitric acid. Sulphuric acid is particularly preferred.

It will be appreciated that the catalyst is present where the reactants of the esterification reaction, i.e. levulinic acid and alcohol, contact each other.

In case of a porous membrane, the two phases will contact each other and form an interface. The esterification will then take place at the interface of the two phases and the catalyst may be present in the aqueous phase, in the alcohol phase, or in both. Alternatively, if the interface is at one of the membrane surfaces or in the membrane, the catalyst may be a heterogeneous catalyst that is positioned on that membrane surface or within the membrane. In case of a porous membrane, the catalyst is preferably a homogeneous catalyst in the aqueous phase.

In case of a dense membrane, i.e. a membrane comprising at least one dense membrane layer, the two phases will not form an interface and the catalyst has to be present either in the alcohol phase or at the membrane surface at the alcohol phase side (permeate side), since only at the alcohol phase side of the membrane both esterification reactants (levulinic acid and alcohol) are present. In that case, the catalyst is preferably a heterogeneous catalyst that is located on the membrane surface at the permeate side. Any heterogeneous esterification catalyst known in the art may be used. Examples of such catalysts are ion-exchange resins, for example Amberlyst (trademark), or acid zeolites. Alternatively, the membrane may be made of a catalytically active material, for example a porous membrane of a catalytically active acid zeolite.

For a homogeneous catalyst, the catalyst concentration is typically in the range of from 0.5 to 20% by weight, preferably of from 1 to 7% by weight, based on the total weight of the phase wherein the catalyst is present.

In order to allow the esterification reaction to take place, the process temperature will be at least 50° C. In order to allow the extraction to proceed, the alcohol phase and the aqueous phase should both be in liquid state. Therefore, the pressure will be at least ambient pressure and the temperature is at most 250° C. It will be appreciated that the higher the process temperature, the higher the process pressure to keep the alcohol and water in liquid state. Preferably, the temperature is in the range of from 60 to 150° C., more preferably of from 80 to 120° C.

Preferably, the pressure in each of the aqueous phase and the alcohol phase is in the range of from 1 to 30 bar (absolute), more preferably of from 1 to 10 bar (absolute), even more preferably of from 1 to 5 bar (absolute).

For a membrane comprising a hydrophobic membrane layer, it is preferred that the pressure of the aqueous phase is slightly higher than that of the alcohol phase, in order to facilitate the aqueous phase into the membrane (in case of a porous hydrophobic membrane) or to facilitate permeation of levulinic acid through the membrane (in case of a dense hydrophobic membrane). For such membranes, the aqueous phase preferably has a pressure that is 1 to 10 bar, more preferably 1.5 to 3 bar, higher than the pressure of the alcohol phase.

What is claimed is:

1. A process for permeation enhanced reactive extraction of levulinic acid from a liquid aqueous phase comprising levulinic acid, wherein the levulinic acid from the aqueous phase is brought into contact with a liquid alcohol phase at esterification conditions in the presence of a catalyst at a temperature in the range of from 50 to 250° C., the aqueous phase and the alcohol phase being separated from each other by a membrane, and an aqueous stream depleted in levulinic acid and an alcohol stream comprising ester of levulinic acid are formed.

2. A process according to claim 1, wherein the aqueous phase comprises 1 to 25 wt % of levulinic acid.

3. A process according to claim 1, wherein the alcohol phase comprises at least 90 wt % alcohol.

4. A process according to claim 1, wherein the alcohol phase comprises an alkyl alcohol with at most 12 carbon atoms.

5. A process according to claim 1, wherein the aqueous phase and the alcohol phase are brought into contact with each other in cross-current flow.

6. A process according to claim 1, wherein the ratio of the mass flow of the alcohol phase and the mass flow of the aqueous phase is in the range of from 1:50 to 1:2.

7. A process according to claim 1, wherein the catalyst is an acid catalyst.

8. A process according to claim 1, wherein the temperature is in the range of from 60 to 150° C.

9. A process according to claim 1, wherein the pressure in each of the aqueous phase and the alcohol phase is in the range of from 1 to 30 bar (absolute).

10. A process according to claim 1, wherein the alcohol in the alcohol phase is water-immiscible.

11. A process according to claim 10, wherein the membrane is a porous membrane.

12. A process according to claim 11, wherein the catalyst is present in the aqueous phase.

13. A process according to claim 10, wherein a hydrophilic membrane is used and the alcohol phase has a pressure that is 1 to 10 bar higher than the pressure of the aqueous phase.

14. A process according to claim 1, wherein the alcohol in the alcohol phase is water-miscible.

15. A process according to claim 14, wherein the membrane comprises a hydrophobic membrane layer that is permeable to levulinic acid.

16. A process according to claim 15, wherein the hydrophobic membrane layer is impermeable to water.

17. A process according to claim 15, wherein the hydrophobic membrane layer is a dense layer that is supported on a porous hydrophilic support layer.

18. A process according to claim 15, wherein the catalyst is a heterogeneous catalyst that is located on the membrane surface at the alcohol phase side.

19. A process according to claim 1, wherein the membrane comprises a hydrophobic membrane layer and the aqueous phase has a pressure that is 1 to 10 bar higher than the pressure of the alcohol phase.

20. A process according to claim 1, wherein the alcohol phase comprises ethanol, 1-butanol, 1-pentanol, 1- or 2-hexanol, 2-ethylhexan-1-ol, or 1-decanol.

* * * * *